(12) United States Patent
Spring et al.

(10) Patent No.: US 12,016,704 B2
(45) Date of Patent: Jun. 25, 2024

(54) MEDICAL IMAGING APPARATUS INCLUDING A GANTRY AND A COUCH HAVING BUILT-IN POWER CONNECTORS

(71) Applicant: CANON MEDICAL SYSTEMS CORPORATION, Tochigi (JP)

(72) Inventors: Mark Spring, Vernon Hills, IL (US); Yoshinori Hamamura, Vernon Hills, IL (US); Kazuya Okamoto, Saitama (JP); Sojiyuuro Kato, Kanagawa (JP); Kazuyuki Soejima, Tochigi (JP)

(73) Assignee: CANON MEDICAL SYSTEMS CORPORATION, Tochigi (JP)

( * ) Notice: Subject to any disclaimer, the term of this patent is extended or adjusted under 35 U.S.C. 154(b) by 136 days.

(21) Appl. No.: 17/701,032

(22) Filed: Mar. 22, 2022

(65) Prior Publication Data
US 2023/0301597 A1  Sep. 28, 2023

(51) Int. Cl.
*G01R 33/36* (2006.01)
*A61B 5/00* (2006.01)
*H02J 7/00* (2006.01)
*H02J 50/12* (2016.01)
*H02J 50/40* (2016.01)

(52) U.S. Cl.
CPC ............ *A61B 5/704* (2013.01); *G01R 33/36* (2013.01); *H02J 7/0068* (2013.01); *H02J 50/12* (2016.02); *H02J 50/402* (2020.01)

(58) Field of Classification Search
CPC ....... A61B 5/704; G01R 33/36; H02J 7/0068; H02J 50/12; H02J 50/402
See application file for complete search history.

(56) References Cited

U.S. PATENT DOCUMENTS

| | | | |
|---|---|---|---|
| 7,634,827 B2 | 12/2009 | Gagneur et al. | |
| 2007/0039101 A1 | 2/2007 | Luginbuhl et al. | |
| 2010/0072997 A1 | 3/2010 | Fischer et al. | |
| 2011/0012598 A1* | 1/2011 | van Helvoort | G01R 33/3692 324/318 |

(Continued)

FOREIGN PATENT DOCUMENTS

| | | |
|---|---|---|
| JP | 2019-92935 A | 6/2019 |
| NL | 8802874 A | 6/1990 |

(Continued)

OTHER PUBLICATIONS

"Wireless Data and Power Link To Detachable Couch", An ip.com Prior Art Database Technical Disclosure, The ip.com Journal, No. IPCOM000259954D, Oct. 2, 2019, 2 pages.

(Continued)

*Primary Examiner* — G. M. A Hyder
(74) *Attorney, Agent, or Firm* — Oblon, McClelland, Maier & Neustadt, L.L.P.

(57) ABSTRACT

A patient couch for use in a medical imaging system that includes a gantry, a power supply unit and a driving unit for positioning the patient couch with respect to the gantry. The patient couch includes at least a first connector for supplying a wireless coil (e.g., a radio frequency (RF) coil for an MRI imaging apparatus) with power. The patient couch is detachably connected to the gantry. The power supply is configured to supply the first connector with power and an optional clock synchronization signal.

14 Claims, 9 Drawing Sheets

(56) References Cited

U.S. PATENT DOCUMENTS

| | | | |
|---|---|---|---|
| 2014/0002085 A1* | 1/2014 | Biber | G01R 33/365 |
| | | | 324/322 |
| 2014/0062485 A1 | 3/2014 | Okamoto | |
| 2014/0097844 A1* | 4/2014 | Tomiha | G01R 33/3692 |
| | | | 324/321 |
| 2015/0028873 A1 | 1/2015 | Dohata et al. | |
| 2016/0077175 A1* | 3/2016 | Mori | G01R 33/56 |
| | | | 324/321 |
| 2018/0003791 A1 | 1/2018 | Kimmlingen et al. | |

FOREIGN PATENT DOCUMENTS

| | | | | |
|---|---|---|---|---|
| WO | WO 2009/150575 A1 | 12/2009 | | |
| WO | WO-2009150575 A1 * | 12/2009 | | G01R 33/3692 |

OTHER PUBLICATIONS

Kevin J. Wu, et al., "Magnetic resonance conditional paramagnetic choke for suppression of imaging artifacts during magnetic resonance imaging", Proceedings of the Institution of Mechanical Engineers, Part H: Journal of Engineering in Medicine, vol. 232, Issue 6, Apr. 24, 2018, pp. 597-604.

Extended European Search Report dated Aug. 11, 2023 in European Patent Application No. 23163503.8, citing references 1 and 15 therein, 7 pages.

Extended European Search Report Issued on Aug. 11, 2023 in European Patent Application No. 23163503.8, citing references 1 and 15 therein, 7 pages.

\* cited by examiner

MEDICAL IMAGING APPARATUS INCLUDING A GANTRY AND A COUCH HAVING BUILT-IN POWER CONNECTORS

BACKGROUND OF THE INVENTION

Field of the Invention

The following relates to the medical imaging apparatuses for holding patients during imaging, and in one embodiment to a couch for use in any of magnetic resonance imaging (MRI), magnetic resonance spectroscopy, computed tomography (CT), and positron emission tomography (PET).

Description of the Related Art

Detachable patient couches are sometimes used with medical imaging scanners, including scanners for magnetic resonance imaging (MRI), computed tomography (CT) or positron emission tomography (PET). Having a detachable couch reduces a number of patient transfers (e.g., from a hospital bed to a stretcher to a scanner compatible stretcher and back again to the hospital bed) as well eases removal of a patient from the scanner and the associated magnetic field at the end of imaging or in an emergency. In addition, a patient may be prepared for the scan on the couch, outside of the scanning room, leading to a more efficient use of the scanner for busy facilities which may use multiple detachable couches in order to separate the patient preparation and scanning tasks.

A number of different shapes and forms of imagers are in use, most having an annular form, with the patient being imaged in the central aperture which extends through the length of the machine. A known imaging system with a corresponding couch is shown in FIG. 1A which depicts a magnetic gantry 103, a bore 110, a support apparatus 105, a couch 130, a base unit 152 and a couch support unit. Both the base unit 152 and the couch support contain gears in order to position the patient which add to the weight of the patient couch. Some MRI imagers have an imaging volume characterized by an open gap bracketed by large plates either on both sides of the patient or on top and underneath the patient. Although annular imagers are shown in figures provided in this description, the presently described technology and the invention applies to imagers of all types.

In magnetic resonance acquisitions, it is sometimes useful to have a radio frequency coil disposed with or near the subject during imaging. Such proximate positioning of a radio frequency coil used for transmitting a magnetic resonance excitation signal, for receiving a magnetic resonance signal, or both, substantially improves radio frequency coupling between the radio frequency coil and the subject. FIG. 1B illustrates internal details of a known couch 130. Shown on the couch 130 are seven coil data ports of which two (135A and 135B) are labeled. As illustrated, the coil data ports carry power, control, and data, and known configurations utilize at least 16 data signals per port. This data traffic, which includes imaging data, results in a large number of data cables (7×16=112) containing data which is passed from the RF coils to coil data ports. The coil data ports (e.g., 135A and 135B) are then connected to an Analog Multiplexer 190 via a series of large cables 140A/140B and then to an Analog to Digital Receiver 194 that carries fewer channels away from the table 130. Alternatively, the configuration could omit the Analog multiplexer 190 and have even more channels going into the Analog to Digital Receiver 194 but would increase the cost of the Analog to Digital Receiver 194.

As a result, one difficulty with local radio frequency coils is the need to separately transfer data from the coils over the large cables 140A/140B. In a typical arrangement, a cable is run from a control unit outside of the scanner into the bore, for example along or inside the subject table to extend along with the tabletop pallet into the bore of the magnetic resonance scanner.

The cables must have a flexible arrangement that accommodates cable slack when the tabletop pallet is withdrawn onto the subject table, and which extends to accommodate the movement of the local coil with the subject into the scanner bore. In addition, one patient may need multiple RF coils for different parts of their body such that more than a single power connector may be contained on the couch. A connector may comprise a female jack, or a male plug either of which can be mounted individually or as part of a slidable electrical connector strip or sliding receptacles.

The table and tabletop pallet arrangement of known magnetic resonance scanners is also a complex assembly typically including a table height adjustment mechanism and a calibrated and automated mechanical translation mechanism for smoothly translating the tabletop pallet from the table into a precise position in the magnetic resonance scanner bore for data acquisition, and for smoothly translating the pallet out of the bore and back onto the table after the data acquisition is complete. Furthermore, integrating a power cable into this complex assembly in a manner which does not interfere with the height adjustment and pallet translation mechanisms add cost, weight, and still further complexity to the system.

The above Background is intended only for general organization of topics within the present invention and is not intended to limit the disclosure of the present invention or any aspect thereof. In particular, subject matter disclosed in the "Background" may include novel technology and may not constitute a recitation of prior art.

SUMMARY OF THE INVENTION

In this disclosure, a number of mechanical components to position the couch within an imaging area (e.g., a magnetic bore) are transferred out of the couch in order to reduce motors and motor controls and thereby reduce the weight of the couch. This includes the motor and positioning hardware to control at least one of the horizontal and vertical positioning of the couch. In addition, the cabling to and from the Radio Frequency (RF) coils is reduced in some embodiments. The RF coils used to receive the RF signals (which are often disposed as local coils at or near the patient on the couch) can be controlled (a) wirelessly or by (b) using data communication over the power cables. Those RF coils may draw power from a variety of electrical connections, such as sliding receptacles or a slidable electrical connector strip placed at the edge of the couch. Embodiments of a couch described herein reduce the potential entanglement and the weight of longer cables and cable retractors as well as addressing safety concerns of possible RF burns from RF cabling and RF connectors close to the patient.

The couch further may provide power to any RF coils which may be needed for the medical imaging. Such coils may nonetheless be referred to as "wireless" coils when they do not include data cables connected thereto (or when they may operate without data cables connected thereto in embodiments which can operate both wired and wirelessly).

Thus, "wireless coils" as used herein may include detachably connected power lines/cables, although the wireless coils also may run on batteries that are recharged by the power connectors described herein. Subject matter disclosed in this "Summary" is not an exhaustive or complete disclosure of the entire scope of the technology or any embodiments thereof.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1A:
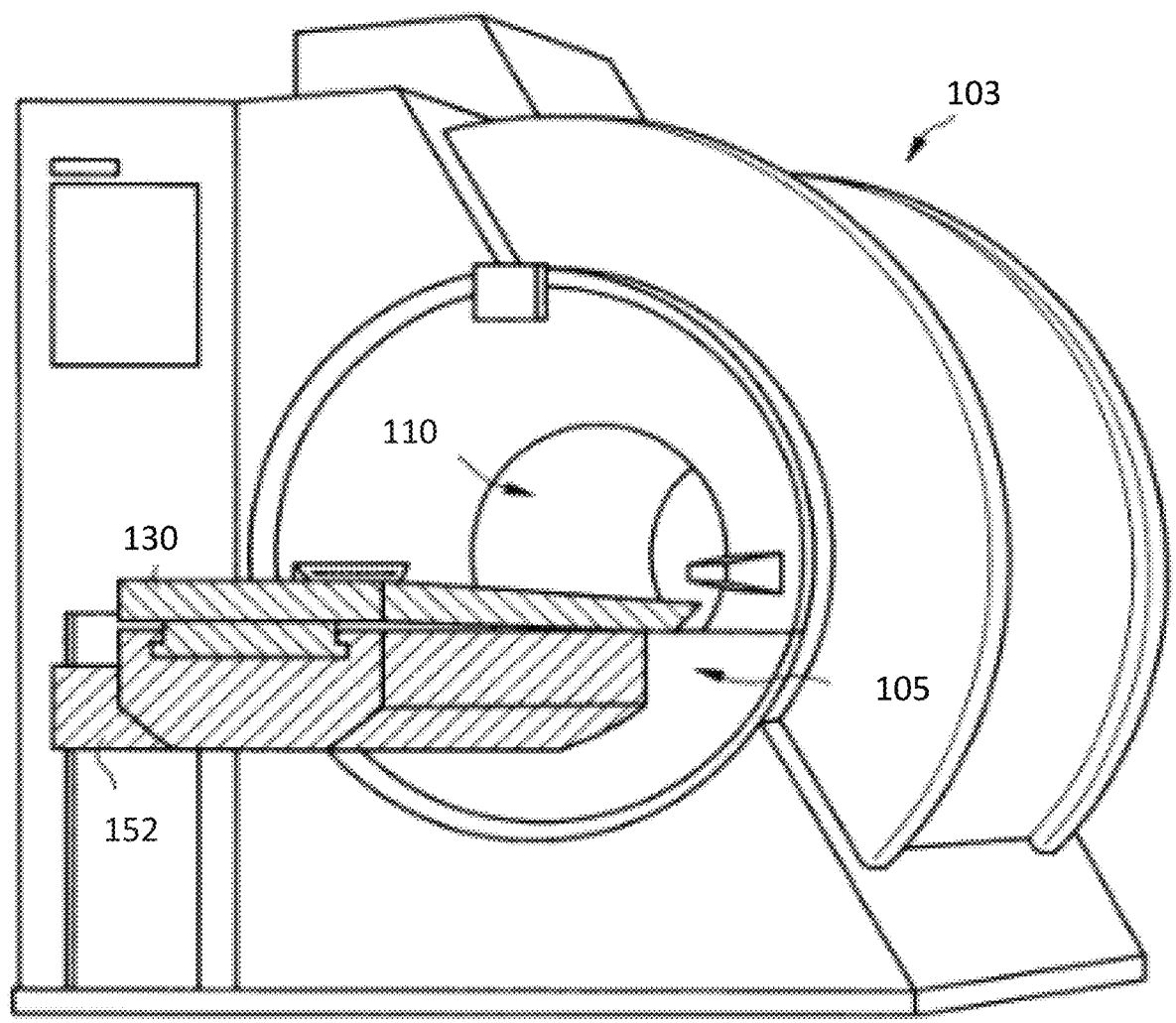
FIG. 1A illustrates a known embodiment of a magnetic resonance imaging system.
Figure 1B:
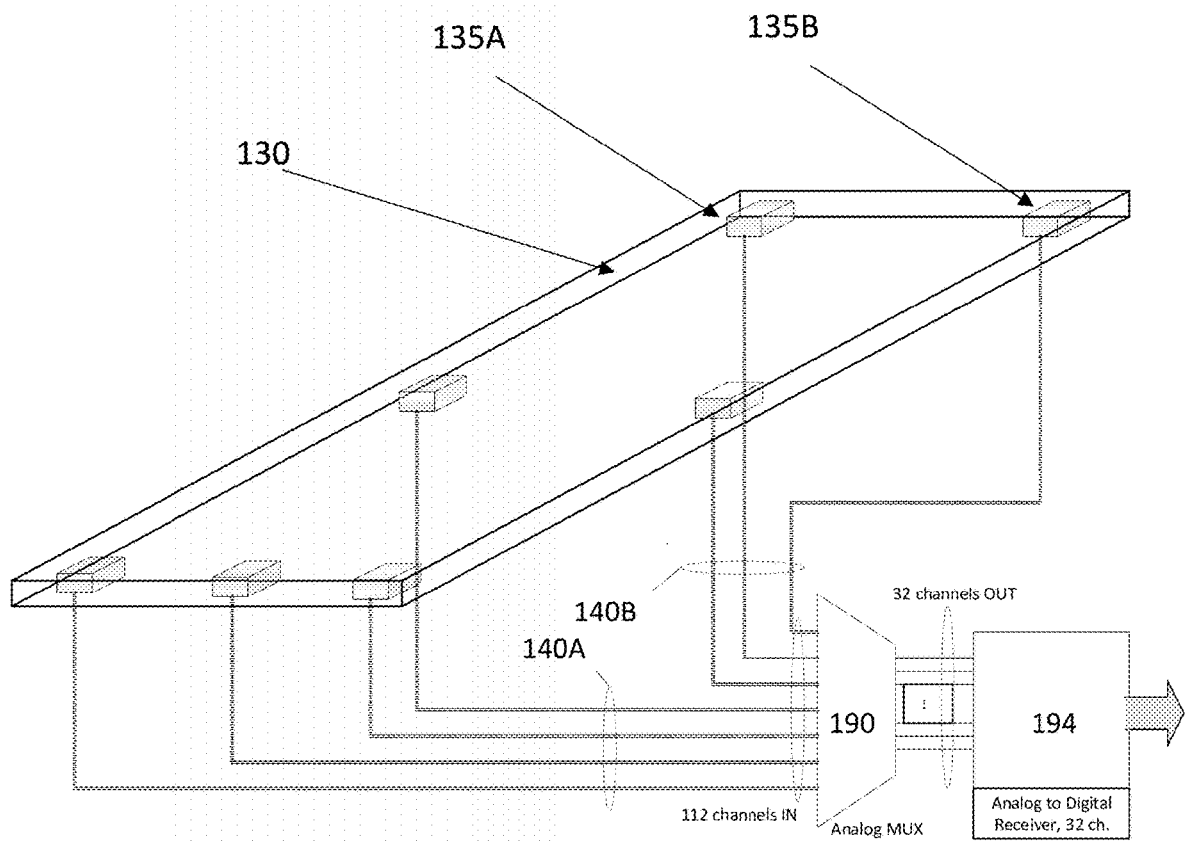
FIG. 1B illustrates internal details of a couch associated with a known embodiment of a magnetic resonance system including large bundles of cables required to route data from various ports within the table.
Figure 2:
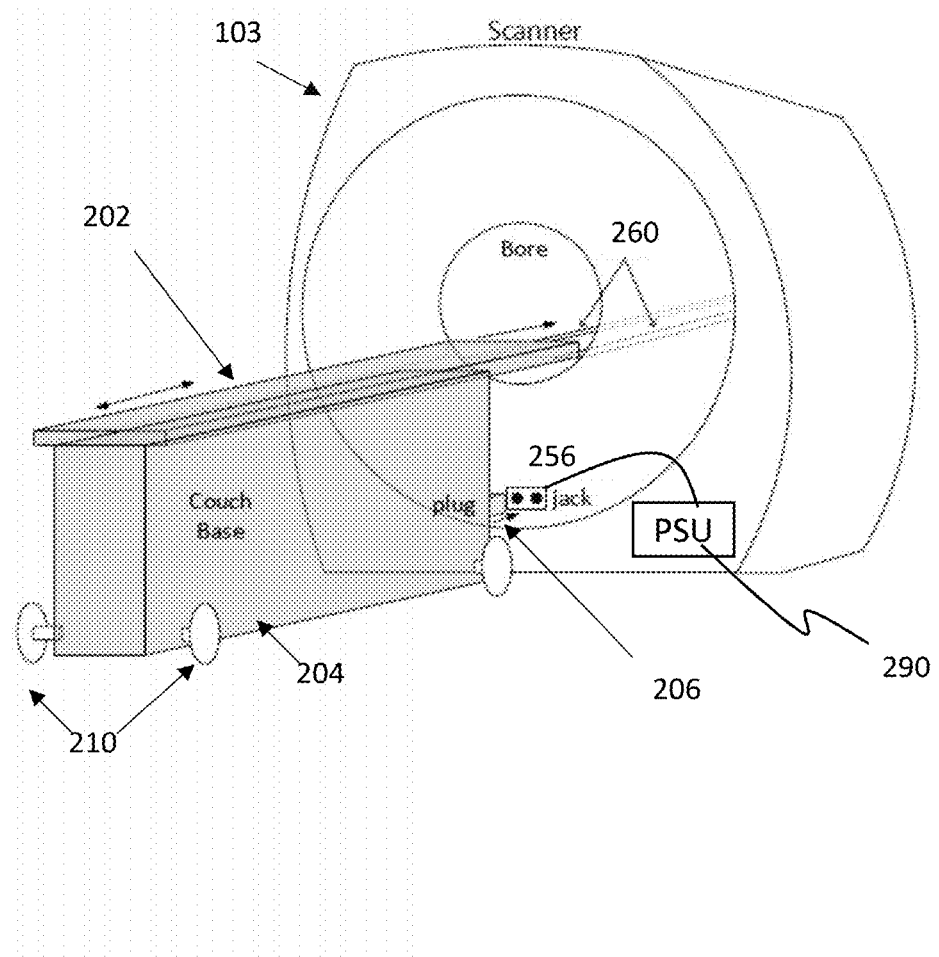
FIG. 2 illustrates an imaging system including a detachable couch according to a first aspect of this disclosure.

Referring now to the drawings, wherein like reference numerals designate identical or corresponding parts throughout the several views. FIG. 2 illustrates an imaging system including the detachable couch 202 according to one embodiment of this disclosure. The magnetic gantry 103 and the bore 110 are shown with the detachable patient couch 202 approaching the bore 110. The top of the couch 202 rests on the couch base 204, and a power connector 206 connected to the couch base is shown as nearly attached to the power connector 256 that receives power from a power supply unit 290. The couch 202 includes transport wheels 210 and rails 260 to guide the top of the couch 202 into the bore 110. In one embodiment, power from the power connector 256 of the gantry 103 is connected (via connector 206) to one or more connectors located at a top of couch 202 by cabling (e.g., cable 304 in FIG. 3) within the couch 202. In another embodiment, power is supplied via a power cable that connectors into the table 202 that may be powered from a power supply unit outside of the room housing the gantry. In another embodiment, the couch 202 contains a battery that is charged (e.g., via a wall socket before the couch 202 is brought into the room with the gantry 103) and that then provides power to RF coils without the couch 202 being connected to power.

Figure 3:
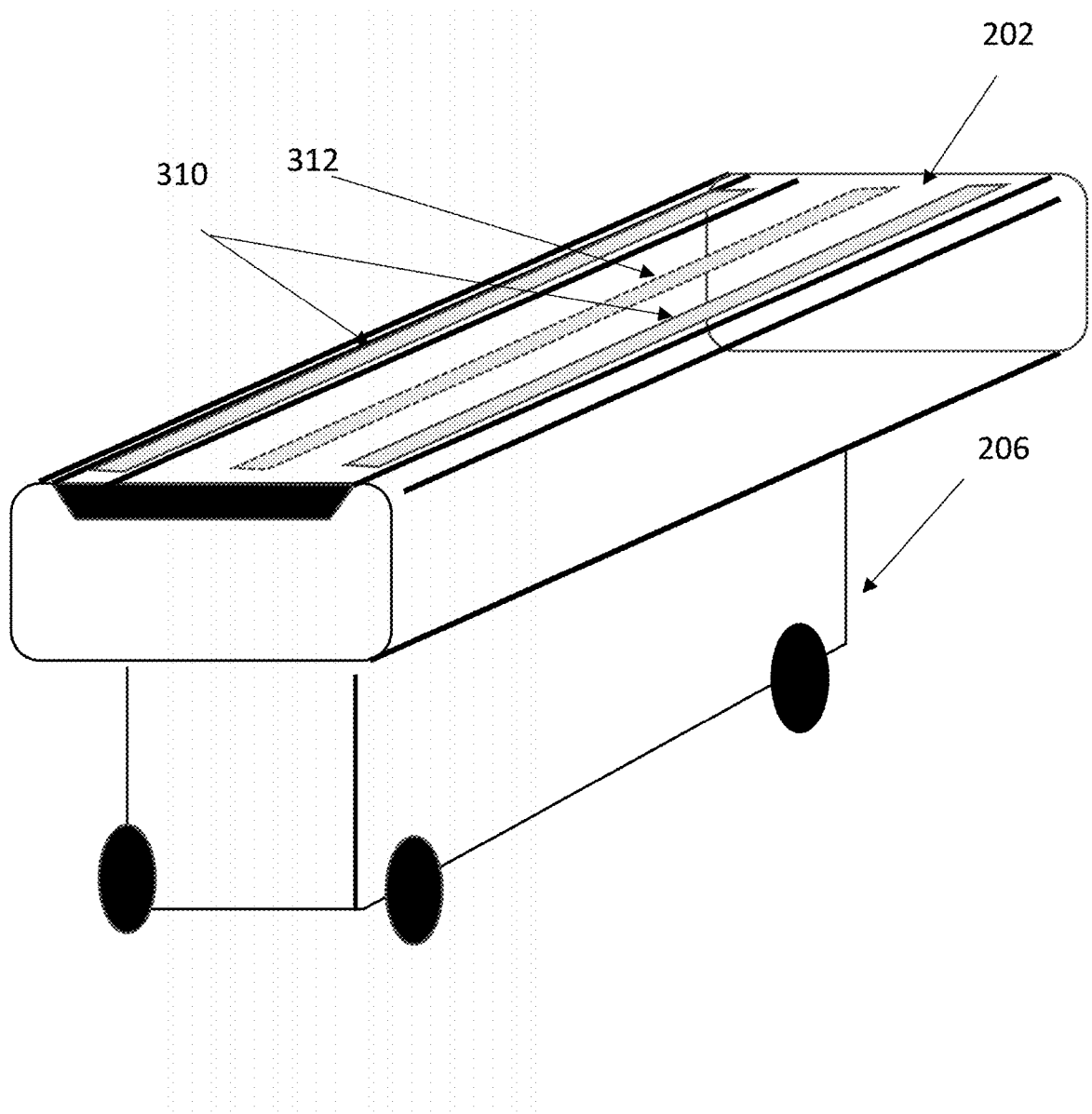
FIG. 3 illustrates an embodiment of this disclosure which generally includes power connection areas as part of a detachable couch.

FIG. 3 illustrates an embodiment in which the power (rather than data) is supplied to one or more power connection areas 310 shown on opposite sides of the top of the couch 202. In an embodiment where power is supplied to the table by the power connector 256 or via the power cable, the table may further include a retractable power cord for keeping the powerlines to the tabletop short and out of the way. The connections within the power connection areas 310 are shown in greater detail in FIGS. 4A-4D. Moreover, although shown as having two power connection areas 310, a couch can have a different number of power connection areas (e.g., one or more than two). The couch 202 also may include, in addition to or instead of power connection areas 310 on the sides, at least one power connection area (not shown) at one end of the couch 202. The couch 202 also may include a power connection area 312 that is underneath a patient when the patient is on the couch 202. Such a power connection area 312 can be used to power RF coils that are underneath the patient during imaging.

Figures 4A, 4B, 4C:
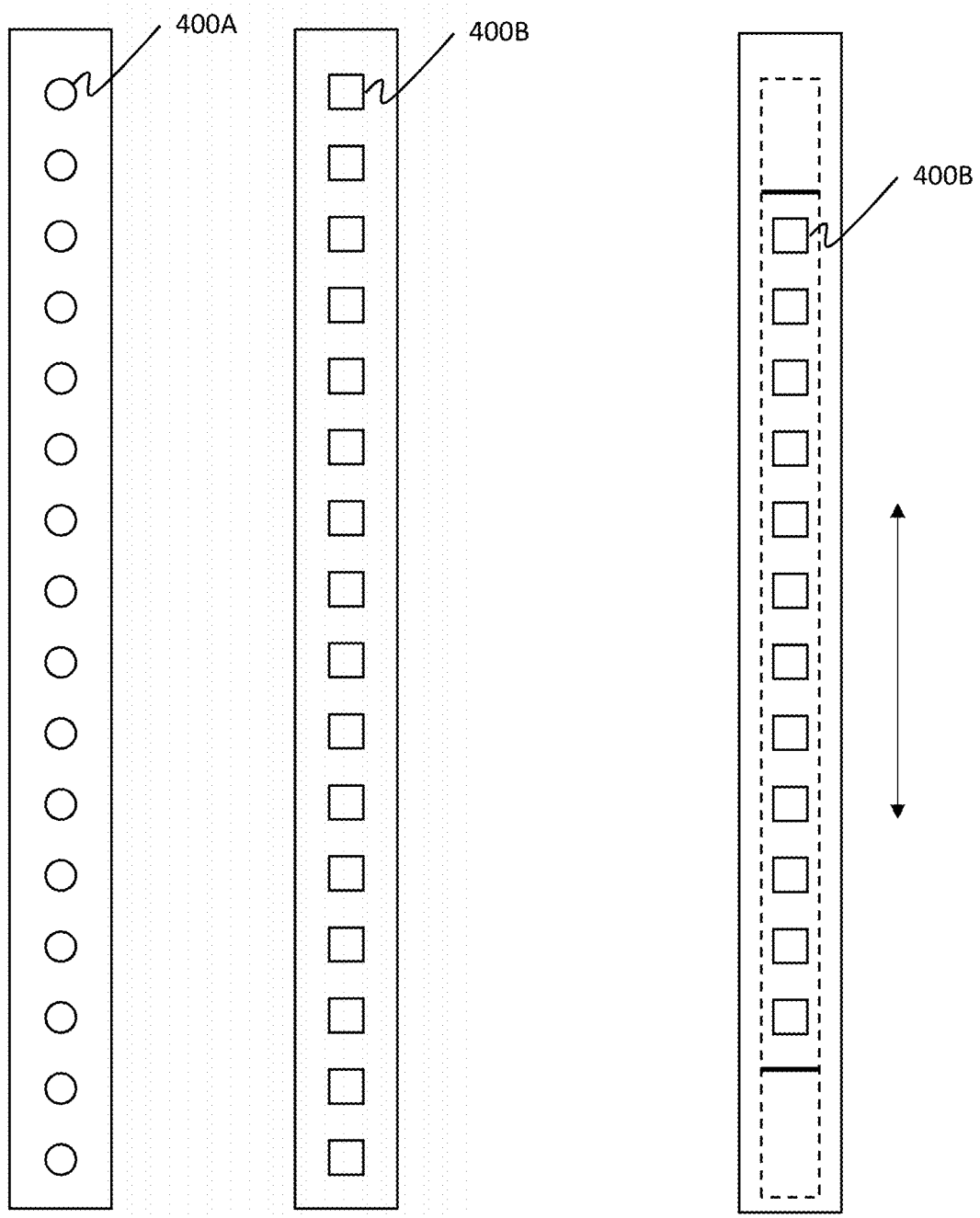
FIG. 4A illustrates an embodiment of a power connection area that utilizes a first series of fixed DC power connectors.
FIG. 4B illustrates an embodiment of a power connection area that utilizes a second series of fixed DC power connectors.
FIG. 4C illustrates an embodiment of a power connection area that uses a slidable electrical connector strip to movably provide DC power connectors.

As shown in FIGS. 4A-4E, a number of different configurations are possible for the power connection areas 310. FIG. 4A illustrates an embodiment of a power connection area 310 that utilizes a first series of fixed power connectors 400A. These connectors may be multi-pronged, such as, for instance +12V, GND, −12V in a three prong configuration, or, for example +12V and GND in a two prong configuration and are designed to carry power (but not data from the RF coils). Although described generally herein as being DC power connectors carrying DC power, an alternate embodiment carries low voltage AC power (e.g., 12V AC) which is converted to DC power within an RF coil using an AC-to-DC converter (e.g., a rectifier). The first series of fixed power connectors 400A are circular connectors into which short power cords can be inserted. In one such configuration, the sides of the power connectors 400A are connected to power of a first polarity (e.g., ground, −5V or −12V, respectively) and the bottom of the power connectors 400A are connected to power of a second polarity (e.g., +5V, +5V, and +12V, respectively). In yet another configuration, additional power connections can be made along the cylindrical side of the power connectors 400A such that a first part of a connector placed in the power connectors 400A contacts a first polarity, a second part of a connector placed in the power connectors 400A contacts a second polarity, and the third part of a connector placed in the power connectors 400A contacts a third polarity. Those of skill in the art will appreciate the similarity with a cylindrical audio connector that includes connections for right and left channels as well as ground (and which may even include a further connection for a microphone).

Alternatively, FIG. 4B illustrates an embodiment of the power connection areas that utilizes a second series of fixed DC power connectors 400B that are square. The sides of the power connectors 400B may be connected to a number of different polarities, such as those described above with respect to FIG. 4A. Additional sides of the power connectors 400B may be connected to connections other than power (e.g., clock). The power connectors 400B also may be keyed to prevent the corresponding cable from being inserted incorrectly. The power connectors 400B also may be connections using standard power connections, e.g., USB-A, USB-B, and USB-C style-ports and may include circuitry for negotiating the power level to be applied from the table to any connected device.

In yet another embodiment, FIG. 4C illustrates an embodiment of a power connection area 310 that uses a slidable electrical connector strip to movably provide DC power connectors 400B. The power connectors 400B remain grouped together but can be slid closer to either end of the couch 202. In a configuration using a slidable power connection area 310 on each side, one side may be slid more toward the end of the couch that goes into the bore while the other side may be slid more toward the end of the couch that is furthest form the bore.

Figure 4D:
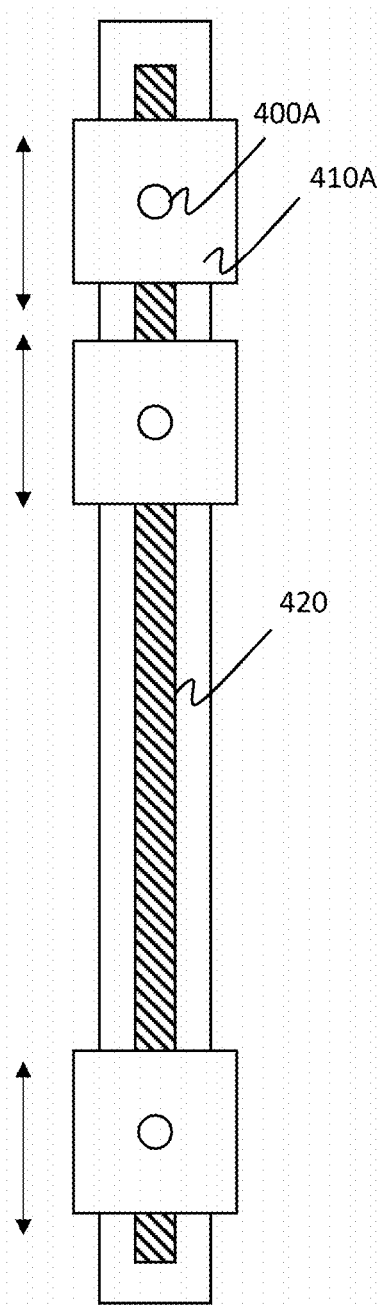
FIG. 4D illustrates an embodiment of a power connection area that uses a series of sliding receptacle connectors to movably provide DC power connectors.
Figure 4E:
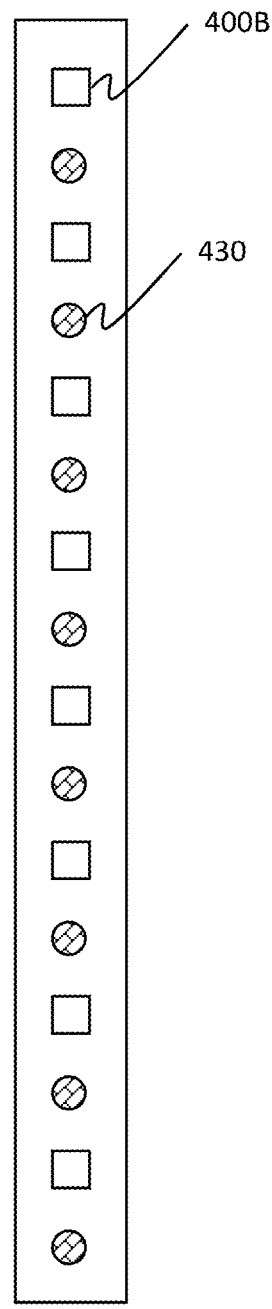
FIG. 4E illustrates an embodiment of a power connection area that utilizes a third series of connectors where the connectors are of different types for carrying different signal types/communications protocols.

FIG. 4D illustrates an embodiment of a power connection area that uses a series of independently slidable sliding receptacle connectors 410 sliding within a channel 420 to movably provide DC power connectors 400B at various locations along one or more sides of the couch 202. In yet another embodiment, as shown in FIG. 4E, the power connection area may include more than one kind of connector, either fixed or movable. For example, the power connection area may include (1) a first set of power connections for providing power at a first level and (2) a second set of connections (e.g., coaxial connections) providing power at a second level which may include additional communicated information (e.g., a clock signal that can be broadcast to all power connectors and that is reliant to interference caused by the transmission of the B1 RF pulse). Using the configurations of FIGS. 4A-4E permits multiple RF coils to be inserted at multiple positions along the top of the couch 202 with a minimum of cabling to the RF coils. In embodiments in which a power cable needs to move to accommodate motion of a power connection area, the couch may further include a power cord retractor and/or power cord tensioner that removes the slack in the power cable to keep it from interfering with the motion of the couch 202. The couch 202 may also derive power from a battery (690 in FIG. 6) which may be integrated with the couch or detachable from the couch in order to minimize weight. The battery may be part of the gantry, part of the couch, or external to both the gantry and the couch.

The cables between RF coils and power connectors can be any of a number of types of cables including, but not limited to, coaxial cable, triaxial cable, parallel cabling, twin axial cables, shielded twisted pair cabling, and unshielded twisted pair. In connections where multiple connectors are to be connected to the same RF coil; combination cables can be made that include two of the cables listed above that are held together with an overmolding. The cables can be permanently attached at the couch side and detachably connected at the RF coils side, detachably attached at the couch side and permanently connected at the RF coils side, or detachably attached at the couch side and detachably connected at the RF coils side. In all configurations, the cables are designed to be as short as possible but preferably without contacting the patient.

Figure 5:
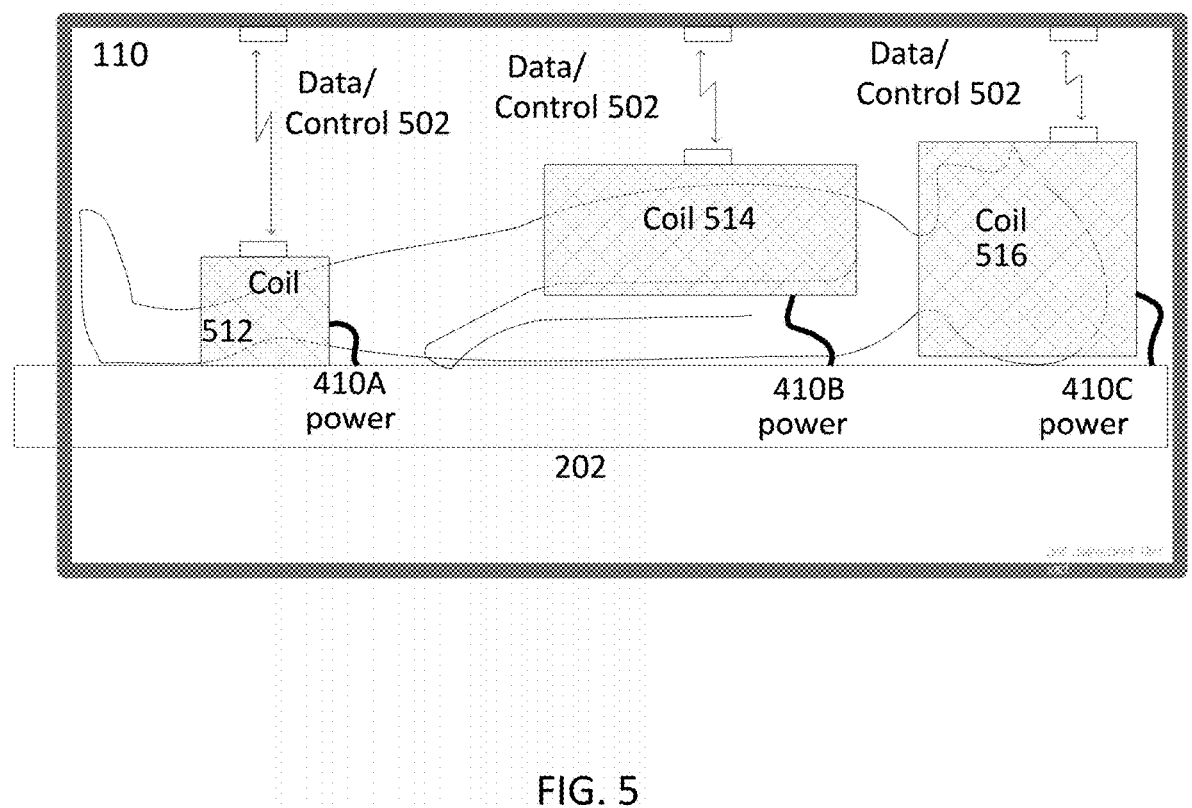
FIG. 5 illustrates a prone patient on a detachable patient couch according to one embodiment.

FIG. 5 illustrates a patient on the top of couch 202, with the top of the couch positioned on top of rails within the bore 110 of the scanning device. The patient is shown with three RF coils which include a surface coil 512, a torso coil 514, and a head coil 516. The coils are electrically connected to the top of couch 202 via three sliding receptacle connectors 410A, 410B, and 410C. In one embodiment, the coils 512, 514, and 516 are powered through the sliding receptacle connectors 410A, 410B, and 410C but controlled wirelessly and image data can also be sent wirelessly 502 to the gantry portion of the system without the data traversing the coil ports. The wireless protocol which may include, for example, IEEE 802.11 Wi-Fi, Bluetooth®, Bluetooth® LE, Near Field Communication, WirelessHART or a variety of other wireless protocols. In another embodiment (not illustrated) the control data and image data can be transferred over the power cables of the detachable couch 202. In this embodiment, a combination of RF chokes and capacitors can be used to separate the power from the data.

Figure 6:
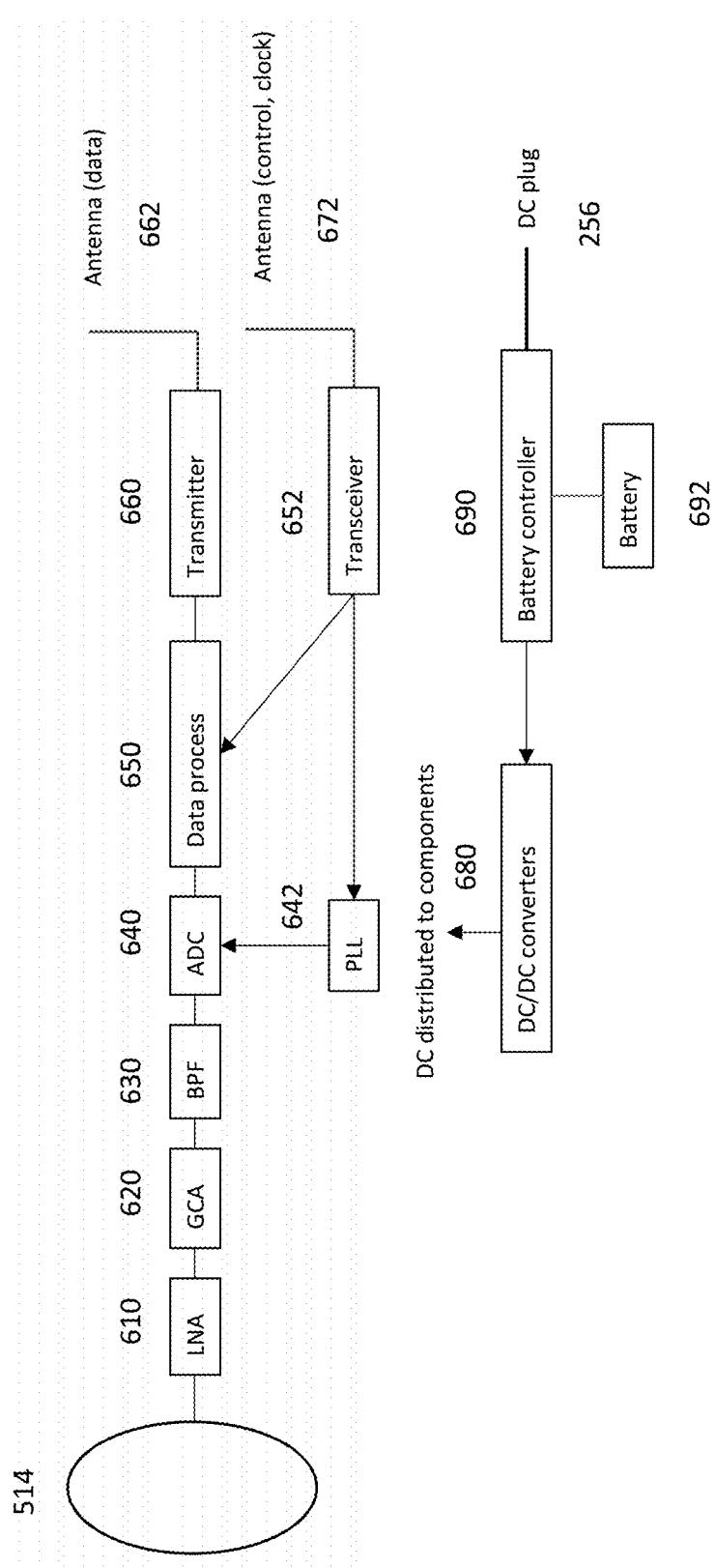
FIG. 6 is a block diagram which illustrates the subcomponents used for transmitting the wireless image data and control data of this disclosure.

FIG. 6 is a block diagram which illustrates the subcomponents used for transmitting the wireless image data and control data of this disclosure. Illustrated is the torso coil 514 connected to a low noise amplifier 610 which may also be a pre-amplifier. The low noise amplifier 610 is connected to either a Variable Gain Amplifier (VGA) or a Gain Control Amplifier (GCA) 620 and the output of the VGA/GCA 620 is passed through a band pass filter (BPF) 630. The output of the BPF 630 is detected and converted by an analog to digital converter (ADC) 640. The ADC 640 passes its output, a digital signal, to a data process module 650. The data process module contains subcomponents such as one or more processors, a RAM or ROM as well as one or more universal asynchronous receiver transmitters (UARTS). The processor module outputs the signal to the transmitter module 660 which outputs the image data 502 over a transmitter antenna 662 to a receiver of the data 502 which may be located adjacent to the bore 110 elsewhere in the gantry 103 or remote from the gantry 103. This is also shown by the upward arrow of the Data 502 in FIG. 5. FIG. 6 also shows a receive antenna 692 which may be used to receive control or clock data as shown by the downward arrows 502 in FIG. 5. In the case of receiving the control or clock data, the data is received by the receive antenna 672 and it is passed to the transceiver 652 and to the data process module 650 before being passed to the ADC 640. Alternately the received control data passes directly to the PLL 642 before going to the ADC 640. The control data passes through the BPF 630, the GCA 620 and the LNA 610 before reaching the RF coil where the data performs a command (such as turning the device on or off or adjusting some other imaging parameter.

Also shown in FIG. 6 are the battery subcomponents, such as the DC connector cable 256, the battery controller 690, the DC/DC converter 680 and the distribution of power to the RF Coil components. This distribution may include, for example, a slidable electrical connector strip 310 or 312 or sliding receptacle connectors 412. An optional slidable electrical connector strip 312 may support RF Coils which may be needed under the patient. In this configuration the RF Coils may be directly connected to the connector strip without use of additional cabling (e.g., using a connector in the underside of the RF coil that connectors directly into the slidable electrical connector strip 312).

Figure 7:
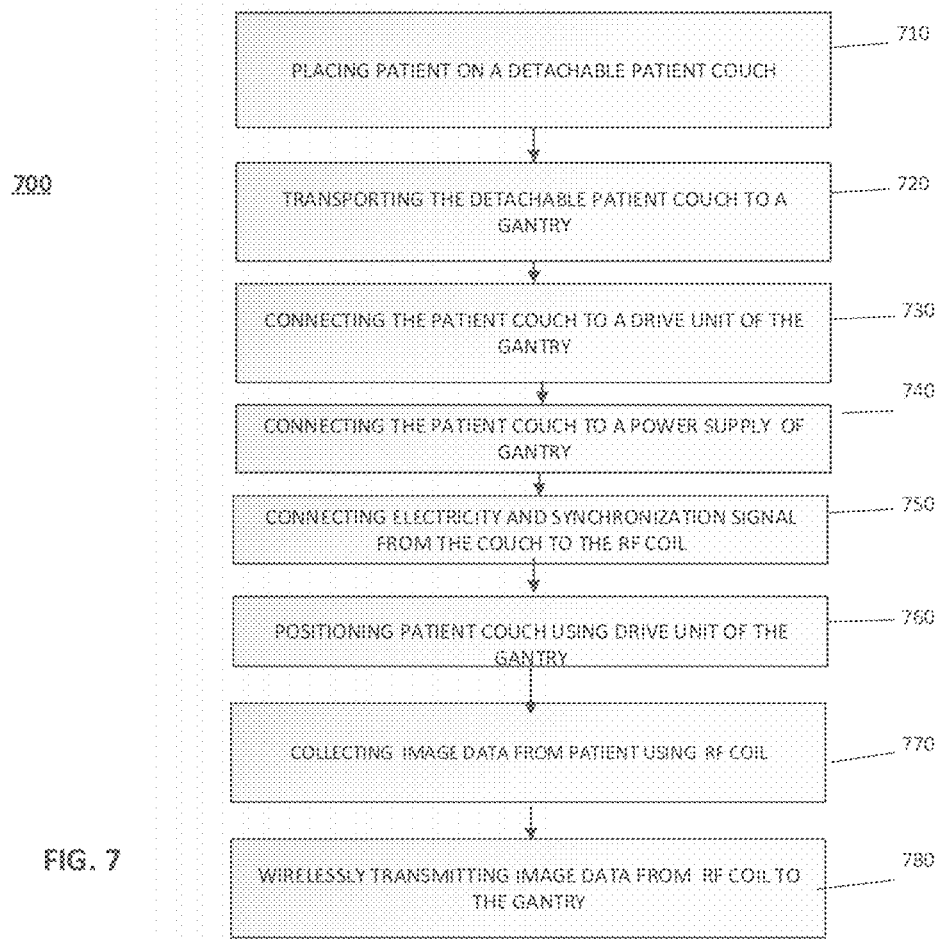
FIG. 7 is a flow diagram which illustrates the method of using the detachable couch with an MRI machine and RF coils that transmit data wirelessly.

FIG. 7 illustrates a flow diagram showing a method 700 of using the detachable couch together with RF coils wirelessly connected to an MRI system where data is transmitted wirelessly to and from the RF coils. Block 710 shows the step of placing the patient on the patient couch 202. This may be done with one or more patients onto multiple couches 200 remote to the gantry in order to make best use of the medical imaging machine. In that case, one or more patients can be prepared for imaging while a previous patient is being imaged. Shown in block 720 is the transporting of the patient to the gantry 103. This can be done with the help of the couch base 204 and the transport wheels

310 shown in FIG. 2. In block 730 the patient couch is connected to a drive unit. This drive unit may be embedded in the couch or integrated with the gantry 103. This may be a drive unit capable of moving the couch 202 either horizontally and/or vertically within the bore 110. In block 740 the electricity base of the patient couch 204 is connected to the power supply of the gantry 103 such as shown in FIG. 2 items 206 and 256. In FIG. 7, block 750, the electricity of the couch, which may carry a synchronization clock is connected to the RF coils. This may be, for example, connecting the RF coils 512 514 or 516 to various points in the slidable electrical connector strip 310 or 312. In block 760 the couch 202 is positioned either horizontally or vertically within the bore 110. In block 762, the RF coils receive control instructions wirelessly which may be, for example to initiate or change the strength or timing of the RF in the RF Coil. In block 770, the image data is collected by the RF Coil and in block 780 the image data is transmitted wirelessly from the RF coils to a receiver located in the gantry or in another room remote from the gantry 103. This might be by use of 4G or 5G cellular, Bluetooth®, IEEE 802.11 Wi-Fi, LoRA®, WirelessHART, ZigBEE® or other wireless protocol.

In another embodiment, the scan control data received in block 762 is not received wirelessly but transmitted over filtered power connections which also would involve a RF Choke to separate the DC electrical power from the signal. In this embodiment, the image data of block 770 may also be transmitted via the power cables.

In another embodiment, a synchronization clock signal may be transmitted to the RF coils over the DC power cables.

Terminology. Terminology used herein is for the purpose of describing particular embodiments only and is not intended to be limiting of the invention.

As used herein, the singular forms "a", "an" and "the" are intended to include the plural forms as well, unless the context clearly indicates otherwise.

It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

As used herein, the term "and/or" includes any and all combinations of one or more of the associated listed items and may be abbreviated as "/".

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the technology.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

Embodiments of the present disclosure may also be as set forth in the following parentheticals:

(1) A medical imaging apparatus including, but not limited to, a power supply unit; a gantry; a couch having a plurality of connectors for respectively supplying a plurality of wireless coils with power from the power supply unit, wherein the plurality of connectors do not receive data from the plurality of wireless coils; and a driving unit configured to position the couch with respect to the gantry.

(2) The medical imaging apparatus of (1), wherein the couch further comprises a connector for connecting to a connector of the gantry, wherein the power supply unit supplies power to the couch via the connector of the gantry and the connector of the couch.

(3) The medical imaging apparatus of (1), wherein the power supply unit is external to the gantry and the couch further comprises a connector for connecting to the power supply unit external to the gantry.

(4) The medical imaging apparatus (1), wherein the power supply unit is a battery housed in the couch and which is rechargeable via at least one of a power connector of the gantry and a power connection external to the gantry and the couch.

(5) The medical imaging apparatus of any one of (1)-(4), wherein the couch is configured to be detachably connected to the gantry.

(6) The medical imaging apparatus of any one of (1)-(5), wherein the plurality of connectors respectively supply the plurality of wireless coils with DC power.

(7) The medical imaging apparatus of any one of (1)-(5), wherein the plurality of connectors respectively supply the plurality of wireless coils with DC power and a clock signal.

(8) The medical imaging apparatus of any one of (1)-(5), wherein the plurality of connectors respectively supply the plurality of wireless coils with AC power.

(9) The medical imaging apparatus of any one of (1)-(8), wherein the plurality of connectors are integrated into sliding receptacle.

(10) The medical imaging apparatus of any one of (1)-(8), wherein a first connector of the plurality of connectors is integrated into a first sliding receptacle and a second of the plurality of connectors is integrated into a second sliding receptacle independently slidable from the first sliding receptacle.

(11) The medical imaging apparatus any one of (1)-(10), further comprising a plurality of cables for respectively connecting the plurality of connectors to the plurality of wireless coils.

(12) The medical imaging apparatus of (11), wherein the plurality of cables comprises a plurality of coaxial cables.

(13) The medical imaging apparatus of (11), wherein the plurality of cables comprises a plurality of triaxial cables.

(14) The medical imaging apparatus of (11), wherein the plurality of cables comprises a plurality of shielded twisted pair cables.

(15) The medical imaging apparatus of (11) wherein the plurality of cables are permanently affixed to the plurality of wireless coils.

(16) The medical imaging apparatus of any one of (1)-(15), wherein the plurality of connectors are connected to the couch adjacent where a patient is configured to lie while being imaged.

(17) The medical imaging apparatus of any one of (1)-(16), further comprising at least one additional connector connected to the couch underneath where a patient is configured to lie while being imaged.

(18) The medical imaging apparatus according to any one of (1)-(17) wherein the driving unit configured to position the couch is integrated with the gantry.

Obviously, numerous modifications and variations of the present invention are possible in light of the above teachings. It is therefore to be understood that within the scope of the appended claims, the invention may be practiced otherwise than as specifically described herein.

The invention claimed is:

1. A medical imaging apparatus, comprising:
a gantry including a power supply unit and circuitry;
a couch having a plurality of connectors to respectively supply, via a corresponding plurality of cables, a plurality of wireless coils with power from the power supply unit so that the plurality of coils are conductively connected to the power supply unit during a scan performed by the medical imaging apparatus, wherein during the scan, each of the plurality of wireless coils transmits data wirelessly to the circuitry such that none of the plurality of connectors receives data from the plurality of wireless coils, and no other connectors are provided on the couch for a wired data connection to the plurality of wireless coils; and
a driving unit configured to position the couch with respect to the gantry.

2. The medical imaging apparatus according to claim 1, wherein the couch further comprises a first connector for connecting to a second connector, the second connector being on the gantry,
wherein the power supply unit supplies power to the couch via the first and second connectors.

3. The medical imaging apparatus according to claim 1, wherein the couch is configured to be detachably connected to the gantry.

4. The medical imaging apparatus according to claim 1, wherein the plurality of connectors respectively supplies the plurality of wireless coils with DC power.

5. The medical imaging apparatus according to claim 1, wherein the plurality of connectors respectively supplies the plurality of wireless coils with DC power and a clock signal.

6. The medical imaging apparatus according to claim 1, wherein the plurality of connectors respectively supplies the plurality of wireless coils with AC power.

7. The medical imaging apparatus according to claim 1, wherein each of the plurality of connectors j integrated into a sliding receptacle.

8. The medical imaging apparatus according to claim 1, wherein a first connector of the plurality of connectors is integrated into a first sliding receptacle and a second of the plurality of connectors is integrated into a second sliding receptacle independently slidable from the first sliding receptacle.

9. The medical imaging apparatus according to claim 1, wherein the plurality of cables comprises a plurality of coaxial cables.

10. The medical imaging apparatus according to claim 1, wherein the plurality of cables is permanently affixed to the plurality of wireless coils.

11. The medical imaging apparatus according to claim 1, wherein the plurality of connectors is connected to the couch adjacent to where a patient is configured to lie while being imaged.

12. A medical imaging apparatus, comprising:
a power supply unit;
a gantry;
a couch having a plurality of connectors to respectively supply, via a corresponding plurality of cables, a plurality of wireless coils with power from the power supply unit, wherein the plurality of connectors do not receive data from the plurality of wireless coils; and
a driving unit configured to position the couch with respect to the gantry,
wherein the plurality of cables comprises a plurality of triaxial cables.

13. A medical imaging apparatus, comprising:
a power supply unit;
a gantry;
a couch having a plurality of connectors to respectively supply, via a corresponding plurality of cables, a plurality of wireless coils with power from the power supply unit, wherein the plurality of connectors do not receive data from the plurality of wireless coils; and
a driving unit configured to position the couch with respect to the gantry,
wherein the plurality of cables comprises a plurality of shielded twisted pair cables.

14. A medical imaging apparatus, comprising:
a power supply unit;
a gantry;
a couch having a plurality of connectors for respectively supplying a plurality of wireless coils with power from the power supply unit, wherein the plurality of connectors do not receive data from the plurality of wireless coils;
a driving unit configured to position the couch with respect to the gantry; and
at least one additional connector connected to the couch underneath where a patient is configured to lie while being imaged.

* * * * *